(12) United States Patent
Huiku et al.

(10) Patent No.: US 9,375,183 B2
(45) Date of Patent: Jun. 28, 2016

(54) METHOD FOR MONITORING SENSOR DEGRADATION, PATIENT MONITOR, PATIENT MONITOR SYSTEM, PHYSIOLOGICAL SENSOR, AND COMPUTER PROGRAM PRODUCT FOR A PATIENT MONITOR

(75) Inventors: Matti Huiku, Espoo (FI); Heikki Joensuu, Vantaa (FI)

(73) Assignee: General Electric Company, Schenectady, NY (US)

( * ) Notice: Subject to any disclaimer, the term of this patent is extended or adjusted under 35 U.S.C. 154(b) by 797 days.

(21) Appl. No.: 13/536,119

(22) Filed: Jun. 28, 2012

(65) Prior Publication Data

US 2014/0005491 A1   Jan. 2, 2014

(51) Int. Cl.
*A61B 5/00* (2006.01)

(52) U.S. Cl.
CPC ....... *A61B 5/7221* (2013.01); *A61B 2560/0276* (2013.01)

(58) Field of Classification Search
CPC .............. A61B 5/1455; A61B 5/7221; A61B 2560/0276; A61B 2560/0266; A61B 2560/028; A61B 2560/0475; A61B 2562/08; A61B 5/085
See application file for complete search history.

(56) References Cited

U.S. PATENT DOCUMENTS

| | | | | |
|---|---|---|---|---|
| 4,942,877 A * | 7/1990 | Sakai et al. | | 600/323 |
| 5,400,267 A * | 3/1995 | Denen et al. | | 702/59 |
| 5,987,343 A * | 11/1999 | Kinast | | 600/323 |
| 6,308,089 B1 * | 10/2001 | von der Ruhr et al. | | 600/338 |
| 6,515,273 B2 | 2/2003 | Al-Ali | | |
| 6,553,241 B2 | 4/2003 | Mannheimer et al. | | |
| 6,675,031 B1 | 1/2004 | Porges et al. | | |
| 6,861,639 B2 | 3/2005 | Al-Ali | | |
| 7,881,761 B2 | 2/2011 | Mannheimer et al. | | |
| 2007/0043282 A1 * | 2/2007 | Mannheimer et al. | | 600/323 |
| 2010/0280343 A1 * | 11/2010 | Huiku | | A61B 5/14551 600/322 |
| 2012/0119661 A1 * | 5/2012 | Muller | | H05B 33/0893 362/382 |

FOREIGN PATENT DOCUMENTS

| | | |
|---|---|---|
| CN | 1542424 | 11/2004 |
| CN | 102151132 | 8/2011 |

OTHER PUBLICATIONS

Office Action for Chinese Patent Application No. 201310267744.5 dated Apr. 5, 2016.

* cited by examiner

*Primary Examiner* — Eric Winakur
(74) *Attorney, Agent, or Firm* — Andrus Intellectual Property Law, LLP

(57) ABSTRACT

A method for monitoring degradation a physiological sensor connected to a patient monitor is disclosed. A patient monitor, a patient monitor system, a physiological sensor, and a computer program product are also disclosed. In order to get an early warning of an imminent breakage or wear out of a physiological sensor and to increase the life time of the sensor without compromising patient safety, history data is collected for at least one sensor feature parameter into a predetermined memory location, wherein the collected history data is indicative of past characteristics of the sensor. The history data is retrieved from the predetermined memory location when the physiological sensor is connected to a patient monitor and a degradation measure indicative of the degree of degradation of the physiological sensor is determined for the physiological sensor based on the history data.

20 Claims, 3 Drawing Sheets

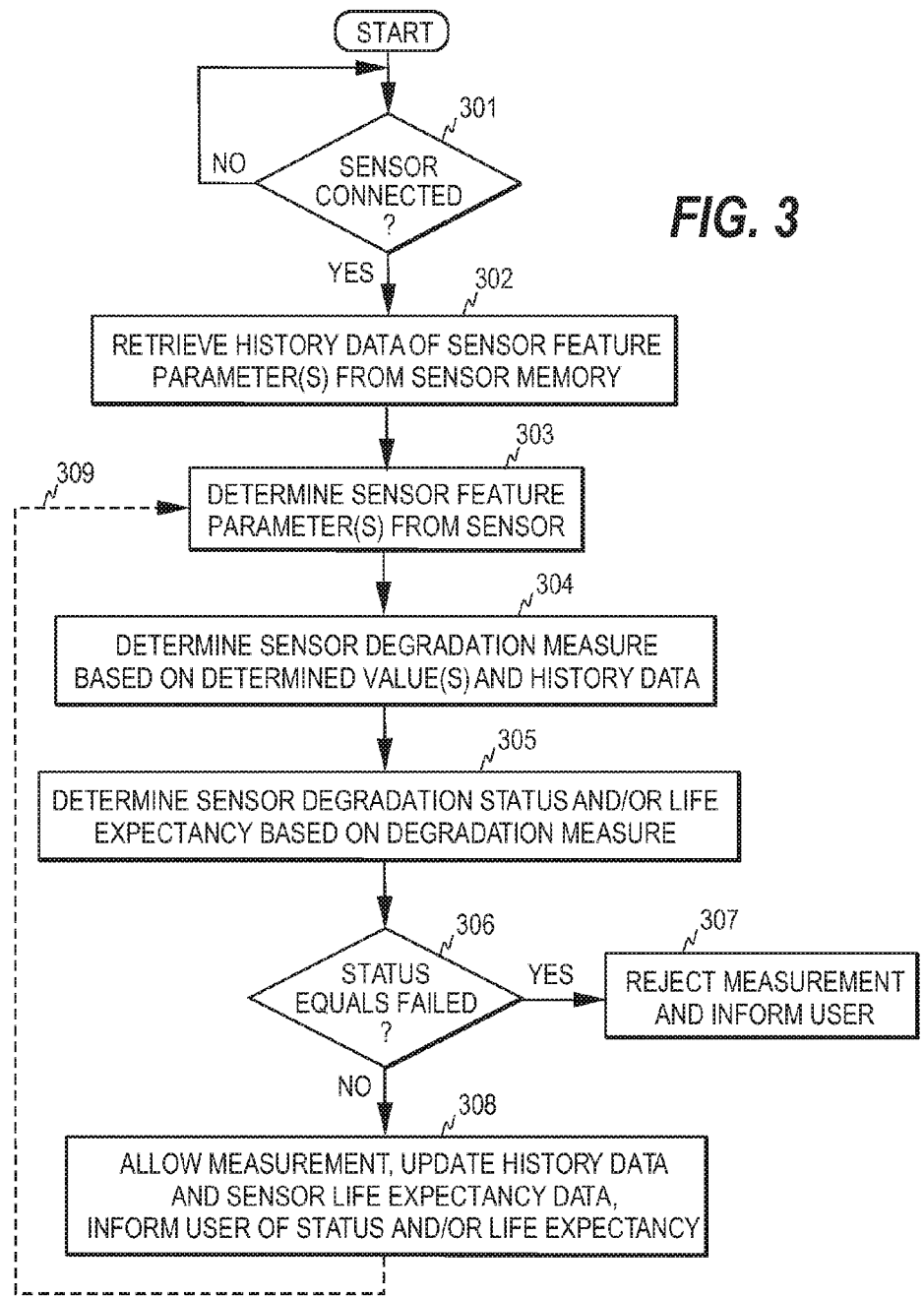

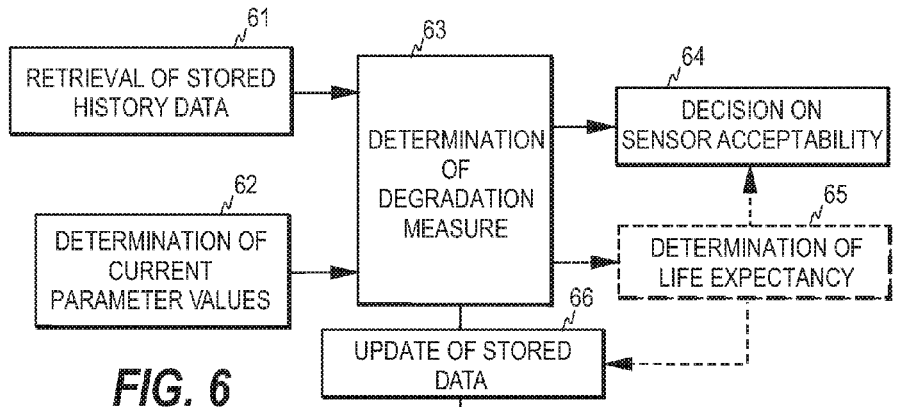
FIG. 6
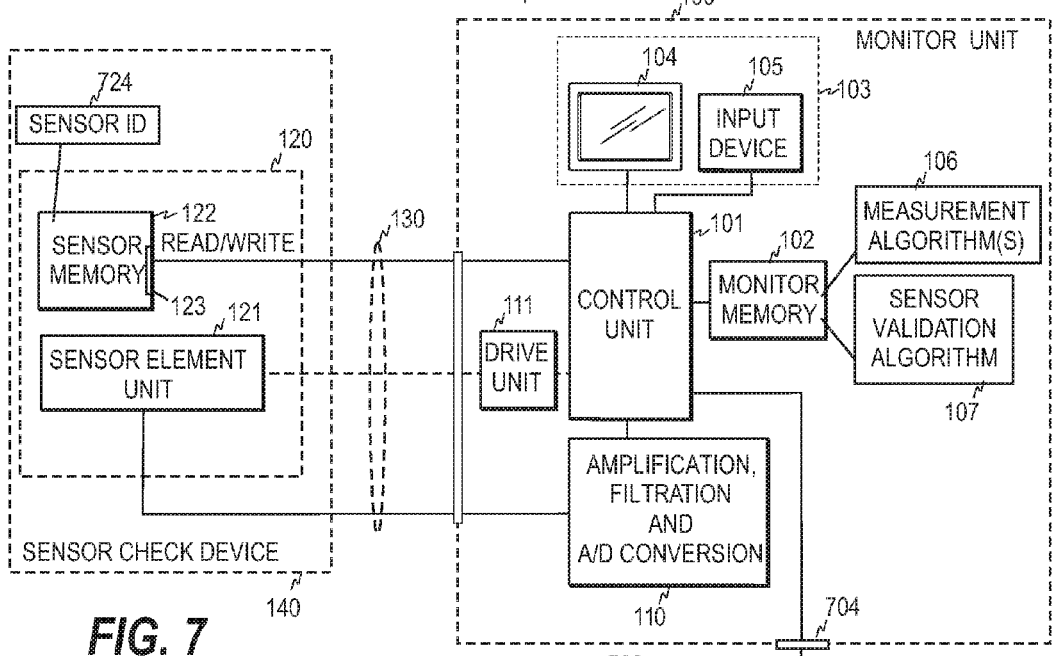
FIG. 7
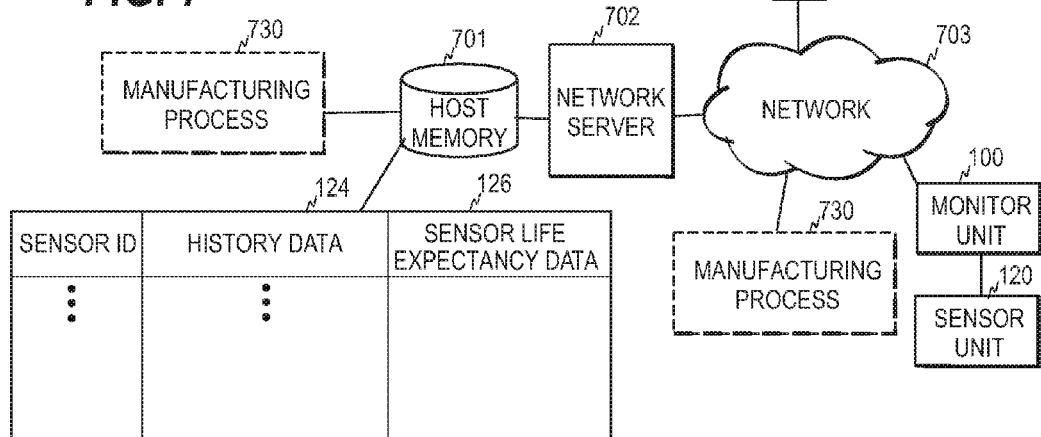

METHOD FOR MONITORING SENSOR DEGRADATION, PATIENT MONITOR, PATIENT MONITOR SYSTEM, PHYSIOLOGICAL SENSOR, AND COMPUTER PROGRAM PRODUCT FOR A PATIENT MONITOR

BACKGROUND OF THE INVENTION

This disclosure relates generally to patient monitors and physiological sensors used for acquiring electrophysiological signals from a subject/patient. More particularly, the disclosure relates to monitoring the degradation of physiological sensors.

A prerequisite of patient care is that accurate and reliable measurements can be made from the patient to evaluate the patient's state. Since a patient monitor connected to a sensor may perform rather complex calculations based on the physiological signals acquired through the sensor and since the results obtained may depend on a variety of parameters related to the sensor, it is important that the sensor fulfills certain quality standards and is thus authorized to be used in the patient monitor for the measurement in question. The use of aged, damaged or low quality sensors may lead to inaccurate and/or unreliable results, which may in turn contribute to incorrect medical decisions and even risk patient safety.

In terms of patient safety, the use of non-authentic, unauthorized and/or counterfeited sensors is also to be prevented, since the cooperation of such sensors with the patient monitor is not tested and the sensors therefore involve the same risks as authentic but aged or low quality sensors.

It is therefore common practice to provide a sensor/monitor system with a detection mechanism that detects aged and/or unauthorized sensors, or with a mechanism that tends to improve the performance level of the sensor. The solutions may be classified into different categories according to the type of data stored in the sensor and according to the way in which data stored in sensor memory is employed. In one solution, the content of the sensor memory is used by a monitor algorithm to make the measurement more accurate. For this, the sensor memory may hold sensor parameters that are relevant to the measurement or provide different calibration coefficient sets for different two or more ranges of certain sensor parameters. The sensor parameters are typically variables that the patient monitor is incapable of measuring, such as LED wavelengths. The sensor memory may also hold operating parameters that prevent the use of the sensor outside a safe operating range. A further solution is to record other information related to the use of the sensor into the sensor memory, such as maximum usage time, expiration data, or warranty date of the sensor. This data may then be used to prevent the use of the sensor when the stored limit value is reached. Instead of measuring cumulated use time, the monitor may also measure the actual total amount of use. This may be carried out by counting the drive pulses transmitted to the sensor, for example.

Although current solutions are able to ensure a high quality sensor operation for the entire life of the sensor, the maximum life time of the sensor is typically determined on a statistical basis so that the risk of a sensor breakage or wear out during the pre-set and fixed life time is low enough in order not to risk patient safety. This also means that the safety margin, i.e. the time between the pre-set maximum life time and the real life time of the sensor is rather long for the majority of sensors. That is, most sensors are discarded even if there would be a considerable amount of life time left at the time of discard. The drawback is emphasized in environments where favorable conditions and good equipment care prolong the life of the sensor.

Consequently, the requirement of patient safety generally and inevitably translates into a shortened life time of the sensor, which means that the end user cannot get a maximal utility out of the sensor.

BRIEF DESCRIPTION OF THE INVENTION

The above-mentioned problem is addressed herein which will be comprehended from the following specification. In the disclosed solution, history data of one or more parameters measured from the sensor is/are used to evaluate the degree of degradation of the sensor during the useful operating life of the sensor. Based on the evaluation, an early warning of an imminent breakage or wear out of the sensor may be given to the end user. Further, the end user can get maximal utility of the sensor without compromising patient safety, since the remaining life time of the sensor may now be adjusted according to the actual condition of the sensor. The history data may comprise, for example, parameter values or statistical variables derived from the parameter values.

In an embodiment, a method for monitoring degradation of a physiological sensor comprises collecting history data for at least one sensor feature parameter into a predetermined memory location, wherein the collected history data is indicative of past characteristics of a physiological sensor, retrieving the history data from the predetermined memory location when the physiological sensor is connected to a patient monitor, wherein the retrieving is performed by the patient monitor, and determining, based on the history data, a degradation measure for the physiological sensor, wherein the degradation measure is indicative of a degree of degradation of the physiological sensor and wherein the determining is carried out in the patient monitor.

In another embodiment, a patient monitor for monitoring a subject comprises a data retrieval unit configured to retrieve history data of at least one sensor feature parameter from a predetermined memory location, wherein the history data is indicative of past characteristics of a physiological sensor connected to the patient monitor, and a degradation determination unit configured to determine, based on the history data, a degradation measure for the physiological sensor, wherein the degradation measure is indicative of a degree of degradation of the physiological sensor connected to the patient monitor.

In a further embodiment, a physiological sensor attachable to a subject for acquiring a physiological measurement signal from the subject comprises a sensor element unit configured to output an electrophysiological signal, a sensor memory storing history data for at least one sensor feature parameter, wherein the history data is indicative of past characteristics of a physiological sensor, and a memory access interface for enabling a patient monitor operably connected to the sensor to retrieve the history data for determination of a degradation measure for the physiological sensor, wherein the degradation measure is indicative of degree of degradation of the physiological sensor.

In a still further embodiment, a patient monitor system for monitoring a subject comprises a memory storing history data for at least one sensor feature parameter, wherein the history data is indicative of past characteristics of a physiological sensor, a data retrieval unit configured to retrieve the history data from the memory when the physiological sensor is connected to a patient monitor, and a degradation determination unit configured to determine, based on the history data, a degradation measure for the physiological sensor, wherein the degradation measure is indicative of a degree of degradation of the physiological sensor.

In a yet further embodiment, a computer program product for monitoring degradation of a physiological sensor comprises a first program product portion configured to retrieve history data of at least one sensor feature parameter from a predetermined memory location, wherein the history data is indicative of past characteristics of a physiological sensor connected to the patient monitor, and a second program product portion configured to determine, based on the history data, a degradation measure for the physiological sensor, wherein the degradation measure is indicative of degree of degradation of the physiological sensor.

Various other features, objects, and advantages of the invention will be made apparent to those skilled in the art from the following detailed description and accompanying drawings.

BRIEF DESCRIPTION OF THE DRAWINGS

FIGS. 2 and 3 illustrate an embodiment of a sensor validation mechanism;

FIG. 6 illustrates an example of the functional units of the patient monitor in terms of sensor validation; and FIG. 7 illustrates another embodiment of the patient monitor system.

DETAILED DESCRIPTION OF THE INVENTION

Figure 1:
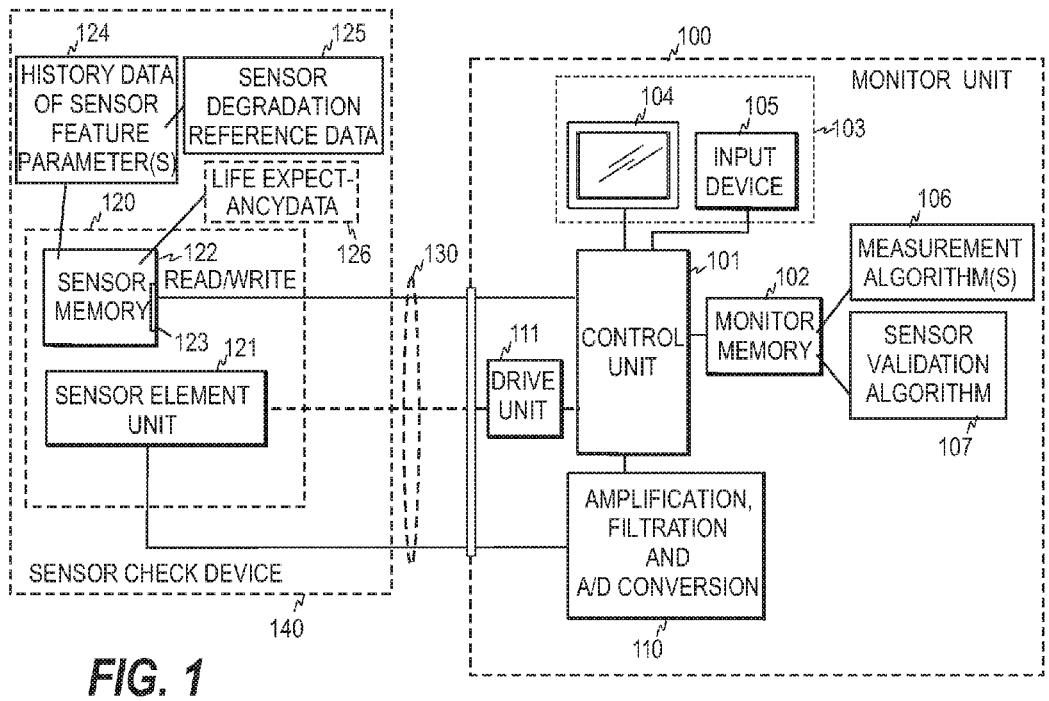
FIG. 1 is a block diagram illustrating an embodiment of a patient monitor system.

FIG. 1 illustrates one embodiment of a sensor and monitor system configured to detect whether a sensor unit connected to a monitor unit is in order and thus also acceptable for the measurement to be initiated. The sensor system of FIG. 1 comprises a monitor unit 100 and a sensor unit 120 attachable to a subject (not shown). The sensor unit 120 is normally connected to the monitor unit 100 through a cable 130, but the connection may also be wireless. It is to be noted that the system is here discussed with respect to one monitor unit 100 and one sensor unit 120 connected to the monitor unit. However, the entire system typically includes several sensor units 120 and one or more monitor units 100. The sensors that can be connected to one patient monitor may be of different types and one sensor may be used in one or more monitors.

The monitor unit 100 may be conceived to comprise three basic elements: a computerized control and processing unit 101, which may be a microcontroller or a microprocessor unit; a memory 102 for the control and processing unit; and a user interface 103, which typically comprises a display 104 and one or more user input devices 105.

A reception branch 110 of the monitor unit is adapted to receive electrophysiological signals from the sensor. The reception branch typically comprises an input amplifier, a filter, and an A/D converter (not shown). The digitized signals output from the A/D converter are supplied to the control and processing unit 101, which processes the signal data and displays the analysis results on the screen of the display. For optical sensors, for example, the sensor may further include a transmitter branch comprising a drive unit 111 for driving the light sources, such as LEDs, of the sensor.

The memory of the control and processing unit holds the measurement algorithm(s) 106 needed to process the data received from the sensor unit.

The sensor unit of FIG. 1 comprises a sensor element unit 121 and a sensor memory 122. The sensor element unit may comprise an array of light sources combined with at least one photo detector or an array of electrodes that may be attached onto the skin of the subject. The sensor memory 122 may be a generic memory from which the monitor may read data and into which the monitor may write data through a memory access interface 123. The sensor memory may thus be a plain (non-volatile) memory with no customized areas/parts, associated intelligence, or data processing capability. The memory may be, for example, an EEPROM or an EPROM memory. The memory holds history data 124 for one or more sensor-specific sensor feature parameters measured from the sensor. The sensor feature parameter is a parameter which is indicative of a given feature related to the condition of the sensor, and which may be used as an evaluation tool for evaluating the degradation of the sensor. As discussed below, in case of an optical sensor the sensor feature parameter may represent, for example, the ratio (rCTR) of two current transfer ratios (CTRs) of the sensor. The history data may include degradation reference data 125 indicative of the condition of the sensor at one or more earlier time instants, i.e. the reference data defines the reference condition against which the current condition of the sensor may be compared to find out the degree of degradation of the sensor. For example, the history data may indicate the condition of the sensor as it was initially in the manufacturing stage of the sensor. This verified initial condition may deviate from the desired initial condition of the sensor.

The sensor memory may further hold sensor life expectancy data 126 that may be indicative of the remaining life time of the sensor. The life expectancy data may be updated in the course of time according to the degree of degradation determined for the sensor.

In addition to the measurement algorithm(s), the memory 102 of the control and processing unit holds a sensor validation algorithm 107 that is executed by the control and processing unit when a sensor unit 120 is connected to the monitor unit 100. The validation algorithm is configured to employ the history data 124 to make a decision on the acceptability of the sensor. For this, the validation algorithm may calculate a degradation measure indicative of the degree of degradation of the sensor. The validation algorithm may also be configured to update the history data and the life expectancy data stored in the sensor. The update may be carried out based on the degradation measure determined.

In a further embodiment, the sensor system may also comprise a sensor check device 140, which is a device to which the sensor unit 120 may be connected to aid the measurement of the sensor feature parameters. For example, the device may be configured to direct the light beams of a reflectance sensor to the photo detector.

FIGS. 2 and 3 illustrate an embodiment of a sensor validation method. FIG. 2 illustrates the steps carried out before the sensor is taken into use, while FIG. 3 illustrates the steps carried out by the control and processing unit 101 of the patient monitor when a sensor is connected to the monitor. The steps of FIG. 2 may be carried out in the manufacturing phase of the sensor or in connection with the first use of the sensor, prior to the actual use of the sensor.

The steps carried out prior to the use of the sensor include the determination of initial value(s) for one or more sensor feature parameter(s) at step 201. The sensor feature parameter(s) serve(s) as indicator(s) of sensor wear. The initial value(s) is/are stored into the sensor memory as reference data for future evaluation of sensor degradation (step 202). That is, the initial value(s) define(s) a reference level by which the sensor degradation may be evaluated. This reference data forms the basis of the history data stored in the sensor. The sensor-specific reference level may deviate from the desired initial condition of the sensor, which is normally common for all sensors of the same type. During subsequent use of the sensor, cf. FIG. 3, the history data is augmented to enable the patient monitor to evaluate the degree degradation based on up-to-date history data. That is, the history data may be collected by several different entities over time.

The steps carried out prior to the commissioning of the sensor may also include storing sensor life expectancy data in the sensor memory (step 203). The life expectancy data may be indicative of the remaining life time of the sensor, such as remaining usage time or number of usage times left. If the sensor leaves the factory with parameters that are inferior to the desired initial state, but good enough to guarantee enough operating hours, the initial life expectancy may be accordingly shorter. During the use of the sensor, the life expectancy data may be updated according to the determined degree of degradation.

Steps 201 to 203 may be carried out by any suitable measuring device used in the manufacturing phase of the sensor to monitor the quality of the sensor. This measuring device may be, for example, a patient monitor or a device that comprises the measuring units of a patient monitor, since the patient monitor is configured to determine the sensor feature parameter in order to find out the degree of degradation.

With reference to FIG. 3, during use the control and processing unit of the patient monitor constantly monitors whether or not a sensor is connected to the monitor unit (step 301). Upon detecting that a sensor is connected to the monitor unit (step 301/yes), the control and processing unit retrieves the history data of the sensor feature parameter(s) from the sensor memory (step 302). The control and processing unit then determines (step 303) the sensor feature parameter(s) from the sensor. That is, in step 303 the control and processing unit measures the parameter(s) similarly as the parameter(s) is/are measured in step 201. Based on the current value(s) and the retrieved history data, the control and processing unit then determines in step 304 a sensor degradation measure indicative of the degree of degradation of the sensor. Based on the measure, the control and processing unit may further determine a degradation status for the sensor (step 305). The degradation measure is typically a number that indicates how far the current parameter value(s) measured in step 302 is/are from the respective initial value(s) measured in step 201. The degradation status is typically a plain language status that discloses the current condition of the sensor to the end user. The degradation status may be, for example, "failed", "in order", or "sensor degrades after 30 operating hours". That is, the degradation status may indicate the usability status or the life expectancy of the sensor. For estimating the current life expectancy of the sensor at step 305, the control and processing unit may retrieve the life expectancy data from the sensor. It is also possible that both the usability status and the life expectancy of the sensor are determined.

If the sensor is aged, the degradation status is "failed" and the measurement is rejected (steps 306 and 307). If the sensor is still usable, the measurement is allowed (step 308). Further, the history data and the life expectancy data are updated and the user may be informed of the usability status and/or the remaining life time of the sensor.

In one embodiment, the sensor is checked only at the beginning of each measurement session. However, in another embodiment the above operation may continue as a background process during the actual measurement, thereby to detect if the sensor degrades during a measurement session. This is illustrated as a dotted arrow 309 in the figure.

In one embodiment, no initial history data, i.e. degradation reference data, is determined in the manufacturing stage, but the sensor memory is left empty. Instead, the degradation reference data may be determined and stored when the sensor is used for the first time. The degradation reference data may also be determined within a certain longer time period since the first use of the sensor, as an average of several measurements, for example. In a further embodiment, the sensor validation process may write, at step 307, a reject code into the sensor memory or delete/erase the sensor memory to ensure that the sensor is removed from use.

In a stripped embodiment, only the degradation measure may be determined and displayed to the user. The measure may be adjusted to a predetermined scale to be informative. If the measure reaches a given threshold, the measurement is rejected.

Figure 4:
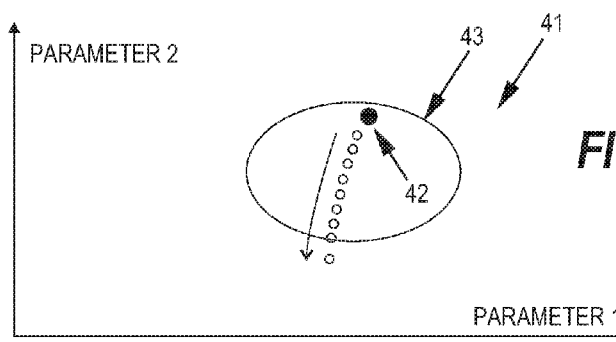
FIG. 4 shows an example of the determination of a measure of sensor degradation.

FIG. 4 illustrates an example of the determination of the degradation measure. It is assumed here that two sensor feature parameters are used. The parameter values obtained are mapped into a two-dimensional parameter space 41, such as an X-Y coordinate system where the x-axis represents the first parameter and the y-axis the second parameter (or vice versa). The data point defined by the initial values of the two parameters is denoted with a black dot 42. If the data point obtained in step 304 is outside an acceptable area 43, the sensor is regarded as "failed" in step 305. In the opposite case, the life expectancy of the sensor may be defined based on the distance of the data point from the fixed reference point 42. In the course of time, the data point obtained for a sensor may move as illustrated by small circles and an arrow.

The sensor feature parameter is typically a parameter that the monitor determines during normal use of the sensor. Further, the sensor feature parameter is typically a continuous value parameter. For example, in case of an optical sensor, the current transfer ratio (CTR) or the ratio of two current transfer ratios (rCTR) may be used as a sensor feature parameter indicative of sensor wear/degradation. CTR indicates the ratio of the detector output current to the LED input current for a LED/detector pair when the input current is supplied to the LED and LED light is directly visible to the detector. Consequently, one or more CTRs or rCTRs may be determined in step 201 and stored in step 202 in the sensor memory. The number of CTRs or rCTRs determined and stored may depend on the number of wavelengths (LEDs) in the sensor. The CTR may be measured when the sensor is off the measurement site (finger or ear) or in sensor calibration mode of the monitor.

Another sensor feature parameter that may be used, provided that the monitor is equipped with the necessary measurement hardware, is forward voltage (also termed forward voltage drop), which is the voltage drop across a LED when current is flowing through the LED. This voltage is indicative of overheating and LED wavelength shift and thus also of wear of the optical components. In addition, the LED voltage may be determined as a function of LED current. This ramp may be indicative of increased resistance in sensor wirings or of bad bonding of the LED on the substrate.

Figure 5:
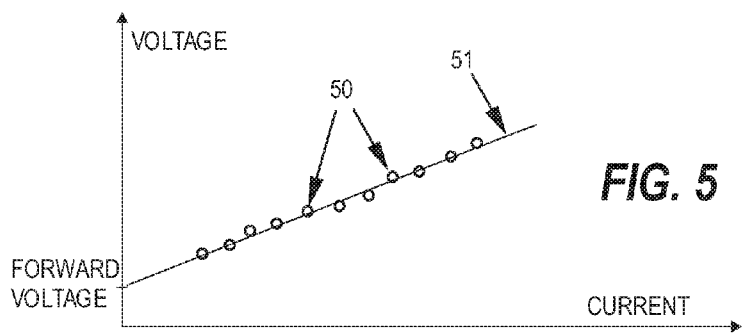
FIG. 5 illustrates the determination of one sensor feature parameter.

FIG. 5 illustrates one embodiment of the determination of forward voltage. In this embodiment, different currents are supplied to a LED and the corresponding voltages are measured. As a result, several data points 50 are obtained. Based on the data points a straight line 51 is fitted through the data points. The voltage value that the line approaches when current approaches zero then indicates the forward voltage. Thus, in this embodiment, the monitor is configured to measure the voltage over and the current through desired LEDs.

A further possible feature parameter is a temperature difference determined based on the resistance of a thermistor used in the sensor. That is, the behavior of a thermistor as part of the thermodynamical system of the sensor can be utilized to determine sensor degradation. The resistance of the sensor thermistor is measured in an initial "cool" state and then in a "warm" state after the sensor has been used so that stable state has been reached. If the sensor or the thermistor is not damaged, the temperature change, i.e. the temperature difference between "warm" and "cool" states, of the sensor should be substantially the same as initially measured in the manufacturing phase or prior to the use of the sensor.

The sensor feature parameter may also be an integer-valued parameter or a Boolean parameter. An integer-valued parameter may indicate, for example, the number of faulty probe or intermittent sensor fault messages received in a time window, if the monitor is provided with sensor diagnostics that monitors faults in sensor operation.

If only one sensor feature parameter is used, the degradation measure may be obtained as the difference of the initial and current values of the parameter. However, history data stored does not necessarily comprise parameter values (provided with time stamps), but statistical variables derived from historical parameter values, such as mean values and standard deviation values of the parameter(s) may be stored instead of plain parameter values. In this case the sensor may be rejected when the mean value of a parameter or the standard deviation of the parameter reaches a respective limit. The sensor may also be rejected, if the parameter value distribution exceeds certain normality limit. For example, the sensor may be rejected when the history parameter values distribute such that the relative portion of the data points further than one standard deviation away from the mean is more than 16%. If multiple parameters are used, the history data stored may cover different time lengths for different parameters. Since the memory size of a cost-effectively implemented sensor is rather limited, typically around 1000 bits, the history data stored in the memory may be in compressed form. In one embodiment, the history data may comprise the following items: initial value(s) of the sensor feature parameter(s), current value(s) of the sensor feature parameter(s), mean of all previously measured values, standard deviation of all previously measured values, and number usage times. The last item enables the update of the mean and standard deviation based on the newest data.

The history data parameters may also be grouped into sets that reflect the degradation of a certain element in the sensor. For example, such data sets may be formed to monitor the degradation of the red LED, infrared LED, or the cable or connector, separately. For monitoring the red LED life expectancy the history data parameters may comprise the red LED forward voltage, the red LED CTR and the red LED internal resistance, which can be determined from the red LED forward voltage measurement as a linear slope of the current-voltage relationship. On the other hand, for evaluating the condition of the cable lead and the connection, the monitor may count the number of short and/or open conditions or the number of "Faulty Probe" messages in a predetermined time interval. The sensor may be rejected when one or more of the sensor elements show an unacceptable condition.

In the above embodiments, the decision on the acceptability is made based on the history data and the current value(s) of the sensor feature parameter(s). However, the decision may also be made based on the history data only, especially if the history data is updated at the end of each measurement session to provide up-to-date history data for the next measurement session. It is also possible that the control and processing unit measures the current value(s) conditionally. If the history data indicates that the sensor is in good condition, the measurement of the current value(s) may be omitted at the beginning of a measurement session. However, if the history data indicates that the sensor is near to the end of its life time, the current value(s) may be measured to get a more accurate view of the current condition of the sensor.

The control and processing unit, which is adapted to execute the sensor validation algorithm, may thus be seen, in terms of the sensor validation, as an entity of different operational modules or units, as is illustrated in FIG. 6. A data retrieval unit 61 is configured to retrieve the history data of the sensor feature parameter(s) in response to the connection of the sensor to the monitor, while a sensor feature determination unit 62 is configured to measure the current value(s) of the sensor feature parameter(s) from the connected sensor, thereby to obtain up-to-date data of the condition of the sensor. As indicated above, the current value(s) may be measured in different stages of a measurement session. A degradation determination unit 63 is configured to determine the degradation measure of the sensor.

A decision-making unit 64 is further configured to make decision on the acceptability of the sensor and thus also on the permission/prohibition of the use of the sensor. The life expectancy, i.e. the remaining life time, may be determined in unit 63 or in separate unit 65 to which the degradation measure is supplied. The decision on the acceptability of the sensor may be made based on the degradation measure or based on the remaining life time. In the stripped embodiment, units 64 and 65 may be omitted. The update functionality may be regarded as a function of a separate update unit 66, which is configured to update the history data and possibly also the life expectancy data.

The unit configured to determine the life expectancy may comprise an autoregressive model, for example. An effective autoregressive model may be created by collecting a large data set of the sensor history parameters for hundreds of sensors at different degradation phases. The autoregressive model is then trained to predict the expected remaining life time of the sensors using the sensor parameter values as independent variables in the model. The model may be created for predicting the remaining life time for a certain sensor component or for the whole sensor.

In the disclosed solution, sensor feature parameter values are used in a novel manner to increase the life of a sensor without compromising patient safety. The sensor feature parameter(s) may be parameter(s) that is/are measured during normal measurement mode of the monitor, such as forward voltage discussed in connection with FIG. 5. In this way, no additional hardware or software is needed in the monitor to determine the parameter value(s) from the sensor, cf. step 302. Based on the sensor's degree of degradation, an early warning of an imminent breakage or wear out of the sensor may be given to the end user. Further, the remaining life time of the sensor may be adjusted according to the actual condition of the sensor, thereby to obtain maximal utility. Moreover, the end user may adjust, based on the evaluation feedback, his/her operating habits so as to extend the life time of the sensor.

In the above embodiments, the necessary information for the sensor evaluation is in the sensor or in the patient monitor, or distributed between the sensor and the monitor. However, at least part of the necessary information may also be stored in an external host memory that may be accessed by several monitors through the network. As is shown in FIG. 7, the host memory 701 may be in conjunction with a network element, such as a database server 702, through which the host memory may be accessed by a plurality of monitor units connected to the same network 703 as the server. The network may be a local area network, such as a hospital network, a wide area network, or the Internet, for example. Each monitor unit is provided with a network interface 704 and a suitable transmission protocol for reading from the host memory 701. In these embodiments, the sensor memory 122 may include a sensor identifier 724 that identifies the sensor connected to the patient monitor. Based on the sensor identifier 724, the patient monitor may retrieve the necessary history data 124 from the host memory 701. The manufacturing process 730 may store the sensor identifier and the initial reference data in the host memory locally or through the network, depending on the locations of the host memory and the manufacturing process. Alternatively, this may be carried out by the patient monitor when the sensor is used for the first time.

A conventional patient monitor may also be upgraded to enable evaluation of sensor degradation according to the above mechanism. Such an upgrade may be implemented, for example, by delivering to the control and processing unit a software unit that includes the entire software system or desired parts thereof. Consequently, the software unit comprises at least a first program product portion configured to retrieve history data of at least one sensor feature parameter from a predetermined memory location and a second program product portion configured to determine, based on the history data, a degradation measure for the physiological sensor. The software unit may also comprise a third program product portion configured to define at least one current value respectively for the at least one sensor feature parameter and update the history data by the at least one current value.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural or operational elements that do not differ from the literal language of the claims, or if they have structural or operational elements with insubstantial differences from the literal language of the claims.

The invention claimed is:

1. A method for monitoring degradation of a physiological sensor, the method comprising:
   collecting history data for at least one sensor feature parameter into a predetermined memory location, wherein the collected history data includes measurements of past operational characteristics of a physiological sensor;
   retrieving the history data from the predetermined memory location when the physiological sensor is connected to a patient monitor, wherein the retrieving is performed by the patient monitor;
   determining, based on the history data, a degradation measure for the physiological sensor, wherein the degradation measure is a measure of the operational degradation of the physiological sensor and wherein the determining is carried out in the patient monitor; and
   determining life expectancy of the physiological sensor based on the degradation measure.

2. The method according to claim 1, further comprising defining at least one current value respectively for the least one sensor feature parameter and updating the history data by the at least one current value, wherein the defining and updating are performed by the patient monitor.

3. The method according to claim 1, further comprising
   deriving a degradation status from the degradation measure, wherein the degradation status discloses the sensor's condition in plain language; and
   informing a user of the patient monitor of the degradation status,
   wherein the deriving and informing are performed by the patient monitor.

4. The method according to claim 3, further comprising deciding on acceptance of the physiological sensor, wherein the deciding is performed by the patient monitor based on one of the degradation measure and the degradation status.

5. The method according to claim 1, wherein the collecting comprises collecting the history data into the predetermined memory location, in which the predetermined memory location is in a memory of the physiological sensor.

6. The method according to claim 1, wherein the collecting comprises collecting the history data, in which the history data includes sensor degradation reference data determined prior to use of the physiological sensor.

7. The method according to claim 1, informing a user of the patient monitor of the life expectancy determined.

8. The method of claim 1, wherein the life expectancy is determined using an autoregressive model of history data from multiple physiological sensors.

9. A patient monitor for monitoring a subject, the patient monitor comprising:
   a data retrieval unit configured to retrieve history data of at least one sensor feature parameter from a predetermined memory location, wherein the history data includes measurement of past operational characteristics of a physiological sensor connected to the patient monitor;
   a degradation determination unit configured to determine, based on the history data, a degradation measure for the physiological sensor, wherein the degradation measure is a measure of operational degradation of the physiological sensor connected to the patient monitor; and
   a decision making unit configured to automatically permit or prohibit use of the physiological sensor based on the degradation measure.

10. The patient monitor according to claim 9, further comprising
    a sensor feature determination unit configured to define at least one current value respectively for the at least one sensor feature parameter; and
    an update unit configured to update the history data by the at least one current value.

11. The patient monitor according to claim 9, wherein the degradation determination unit is further configured to
    derive a degradation status from the degradation measure, wherein the degradation status discloses the sensor's condition in plain language; and
    inform a user of the degradation status.

12. The patient monitor according to claim 11, wherein the decision-making unit automatically permits or prohibits use of the physiological sensor based on the degradation status.

13. The patient monitor according to claim 9, wherein the patient monitor is further configured to
    determine life expectancy of the physiological sensor based on the degradation measure; and
    inform a user of the patient monitor of the life expectancy.

14. The patient monitor according to claim 13, the patient monitor comprises a predefined model configured to predict the life expectancy.

15. A physiological sensor attachable to a subject for acquiring a physiological measurement signal from the subject, the physiological sensor comprising:
- a sensor element unit configured to output an electrophysiological signal;
- a sensor memory storing history data for at least one sensor feature parameter, wherein the history data includes measurements of past operational characteristics of a physiological sensor;
- a memory access interface for enabling a patient monitor operably connected to the sensor to retrieve the history data for determination of a degradation measure for the physiological sensor, wherein the degradation measure is a measure of the operational degradation of the physiological sensor, and for determination of a life expectancy of the physiological sensor based on the degradation measure; and
- wherein the sensor memory further stores the life expectancy of the physiological sensor.

16. The physiological sensor according to claim 15, wherein the history data includes at least one statistical variable derived from previous value distribution of the at least one sensor feature parameter.

17. A method for monitoring degradation of a physiological sensor, the method comprising:
- collecting history data for at least one sensor feature parameter into a predetermined memory location, wherein the collected history data includes measurements of past operational characteristics of a physiological sensor;
- retrieving the history data from the predetermined memory location when the physiological sensor is connected to a patient monitor, wherein the retrieving is performed by the patient monitor;
- determining, based on the history data, a degradation measure for the physiological sensor, wherein the degradation measure is a measure of the operational degradation of the physiological sensor and wherein the determining is carried out in the patient monitor;
- determining acceptability of the physiological sensor based on the degradation measure; and
- prohibiting use of the physiological sensor if the physiological sensor is not acceptable.

18. The method of claim 17, wherein the degradation measure is a difference between two history data values, and use of the physiological sensor is prohibited if the degradation measure exceeds a predetermined value.

19. The method of claim 18, wherein the sensor feature parameter is forward voltage drop across an LED in the physiological sensor, the history data includes a linear slope of the current-voltage relationship, and the degradation measure is a change in the linear slope.

20. The method of claim 17, wherein the degradation measure includes one of a mean or a standard deviation of at least a portion of the history data, and use of the physiological sensor is prohibited if more than a predetermined number of history data values are more than one standard deviation away from the mean.

* * * * *